US00PP29252P3

(12) United States Plant Patent
Maillard et al.

(10) Patent No.: US PP29,252 P3
(45) Date of Patent: Apr. 24, 2018

(54) CHERRY TREE NAMED 'ROSALOLAM'

(50) Latin Name: ***Prunus avium* (L.) L.**
Varietal Denomination: ROSALOLAM

(71) Applicant: AGRO SELECTIONS FRUITS, Elne (FR)

(72) Inventors: Arsene Maillard, Elne (FR); Laurence Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 0 days.

(21) Appl. No.: 15/330,880

(22) Filed: Nov. 10, 2016

(65) Prior Publication Data

US 2017/0156245 P1 Jun. 1, 2017

(30) Foreign Application Priority Data

Nov. 27, 2015 (QZ) ..... PBR 2015/2860

(51) Int. Cl.
*A01H 5/08* (2006.01)

(52) U.S. Cl.
USPC ..... Plt./181

(58) Field of Classification Search
USPC ..... Plt./181
CPC ..... A01H 5/085
See application file for complete search history.

*Primary Examiner* — Kent L Bell
(74) *Attorney, Agent, or Firm* — Westerman, Hattori, Daniels & Adrian, LLP

(57) ABSTRACT

A new and distinct variety of cherry tree denominated 'ROSALOLAM' has fruits that ripen early in the season, with big size and two colored fruit skin, very firm, and with a good flavor and eating quality; the fruit is further characterized by its good handling and storage qualities.

2 Drawing Sheets

Latin name of the genus and species of the plant claimed: *Prunus avium* (L.) L.

Variety denomination: 'ROSALOLAM'.

This application claims priority of Community plant variety right No. 2015/2860 filed on Nov. 27, 2015 (Nov. 27, 2015) which is hereby incorporated by reference in its entirety.

BACKGROUND OF THE NEW VARIETY

Field of the Invention

In the field of plant genetics, we conduct an extensive and continuing plant-breeding program including the organization and reproduction of orchard trees, among which peaches, nectarines, apricots, apples, and cherries are exemplary. It was against this background of our activities that the present variety of cherry tree was originated and reproduced by us in our experimental orchard located near Elne, Pyrénées Orientales, France.

ORIGIN OF THE VARIETY

The present invention relates to a new a distinct variety of cherry tree *Prunus avium* L. which has been given the variety denomination 'ROSALOLAM'. This tree produces fruits with a long shelf life without alteration both on the trees after growth completion and after harvesting, very good eating quality with a cream colored flesh, and for fresh market in June in the Pyrénées Orientales department, France.

Contrast is made to 'RAINIER' cherry tree (not patented) for reliable description. 'ROSALOLAM' is a promising candidate for commercial success in that it produces very attractive fruits having a long shelf life.

The present new variety of cherry tree (*Prunus avium* L.) was developed by us in our experimental orchard located in France. 'ROSALOLAM' cherry tree originated in a cultivated area of the South of France, in the Pyrénées-Orientales department where it was also tested. This zone also called Roussillon is subject to a Mediterranean climate. The winter is generally sweet that is to say the total amount of cold hours lower than 7° C. (Celsius) varies from 600 hours to 1200 hours. The summer is hot and dry. that is to say the total amount of sunshine hours is an average of 2400 hours to 2800 hours per year. The prevailing wind is called "Tramontane": it dries the air and clear the sky from cloud but its intensity can be strong and affect the harvest, fruits quantity and/or quality. Marine moisture does not affect the place. Precipitations are irregular through the year and from one year to another. The amount of rainy days does not exceed 80 days per year and are mostly found in Spring and Autumn. In May and October, very intense precipitations occasionally happen and the summer is dry with a few thunderstorms.

The 'ROSALOLAM' variety resulted from an open pollination of the cherry tree variety named 'RUBILAM' (U.S. Plant Pat. No. 23,798) which was used as the seed parent. Thus, the pollen parent is unknown.

The 'ROSALOLAM' variety was obtained by hybridizing and propagated by grafting on a 'Maxma14' (non-patented) rootstock trees. It has been determined to have unique tree and fruits characteristics making it worthy for commercial fresh fruits production. There are no known effects of the standard rootstock tree set forth above on the scion cultivar. Asexually propagated plants remained true to the original tree and all characteristics of the tree and the fruit were transmitted. The plant was asexually reproduced by us in Les Régalines, Route d'Alenya, La Prade de Mousseillous, 66200 ELNE, Pyrénées Orientales, France. More particularly, the plant was reproduced by grafting.

Compared to its female parent 'RUBILAM' variety (U.S. Plant Pat. No. 23,798), which is a red cherry tree, the new variety 'ROSALOLAM' is considered as a two-colored cherry tree.

The flowers of the new variety 'ROSALOLAM' bloom approximately one week earlier than the flowers of the variety named 'RUBILAM'.

Regarding the ripening period, the fruits of the new variety 'ROSALOLAM' ripen generally earlier than the fruits of the 'RUBILAM' variety, but it depends on the year.

For the new variety 'ROSALOLAM', the color of the fruits is considered two-colored, with a pinkish red color covering 60% of the fruit skin surface (RHS RED GROUP 46 A) on an orange cream background covering 40% of the fruit skin surface (RHS YELLOW GROUP 11 A or RHS YELLOW GROUP 13 C). In comparison, the 'RUBILAM' variety produces fruits that show a color 100% bright red (RHS RED PURPLE GROUP 59 A or RHS RED PURPLE GROUP 59 B).

Regarding the characteristic related to the stone size, the stone of the new variety 'ROSALOLAM' is considered medium whereas the stone of 'RUBILAM' is small to medium in size. The stone shape of the new variety 'ROSALOLAM' is round to ovate whereas the 'RUBILAM' variety has a stone which is considered broad and elliptic.

The color of the flesh of the new variety 'ROSALOLAM' is considered yellow (RHS YELLOW 11 B or RHS YELLOW 11 C) and turns to an orange yellow color (RHS YELLOW ORANGE 18 B) at ripening time. In comparison, the flesh color of the 'RUBILAM' variety is red when the fruits are mature (RHS RED GROUP 53 A or RHS RED GROUP 53 B).

The shape of the 'ROSALOLAM' fruits is considered reniform whereas the fruit shape of 'RUBILAM' is reniform rounded.

SUMMARY OF THE NEW VARIETY

The new variety 'ROSALOLAM' produces fruits of big size, firm, with a semi-sweet flavor, low acidity, and a pinkish red color of skin on an orange cream background. The blooming period is medium for the variety, generally from the end of March to beginning of April. The maturity period is medium, generally from the middle of May to beginning of June in the South of France. However, it was observed that its early date of blooming and maturity seems to be highly dependant on climatic conditions.

BRIEF DESCRIPTION OF THE DRAWINGS

The accompanying photographs show typical specimens of the new variety as depicted in color as nearly true as is reasonably possible in color illustrations of this character. These specimens were obtained at our experimental orchard located near Elne, South of France.

Figure 1:
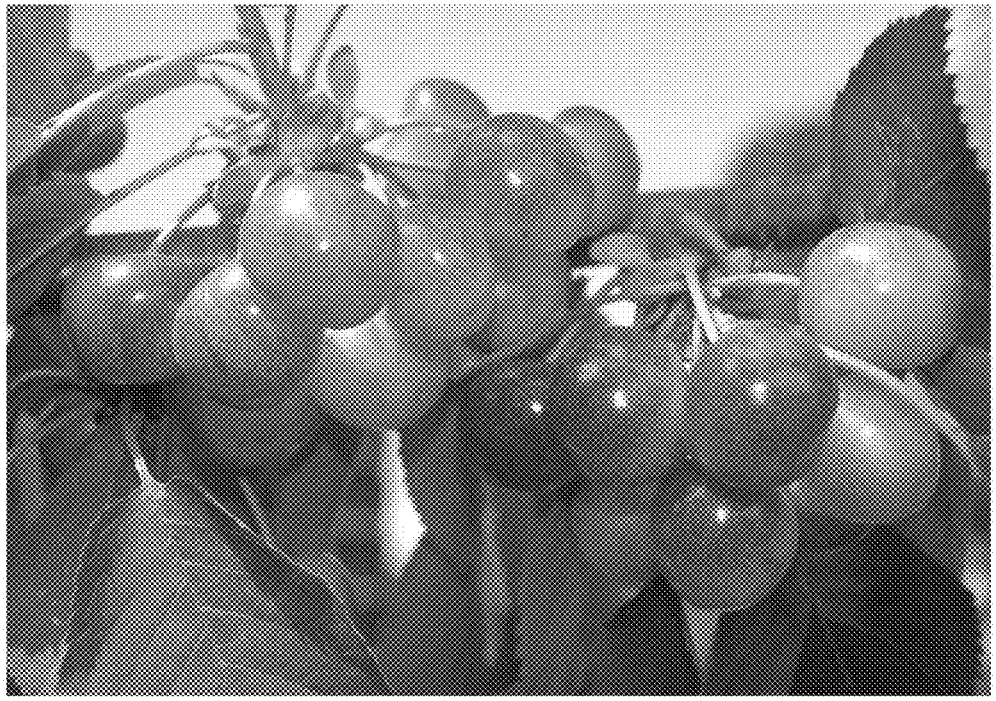
FIG. 1 is a color photograph which shows a view of a tree of the new variety in orchard, with a branch bearing fruits.
Figure 2:
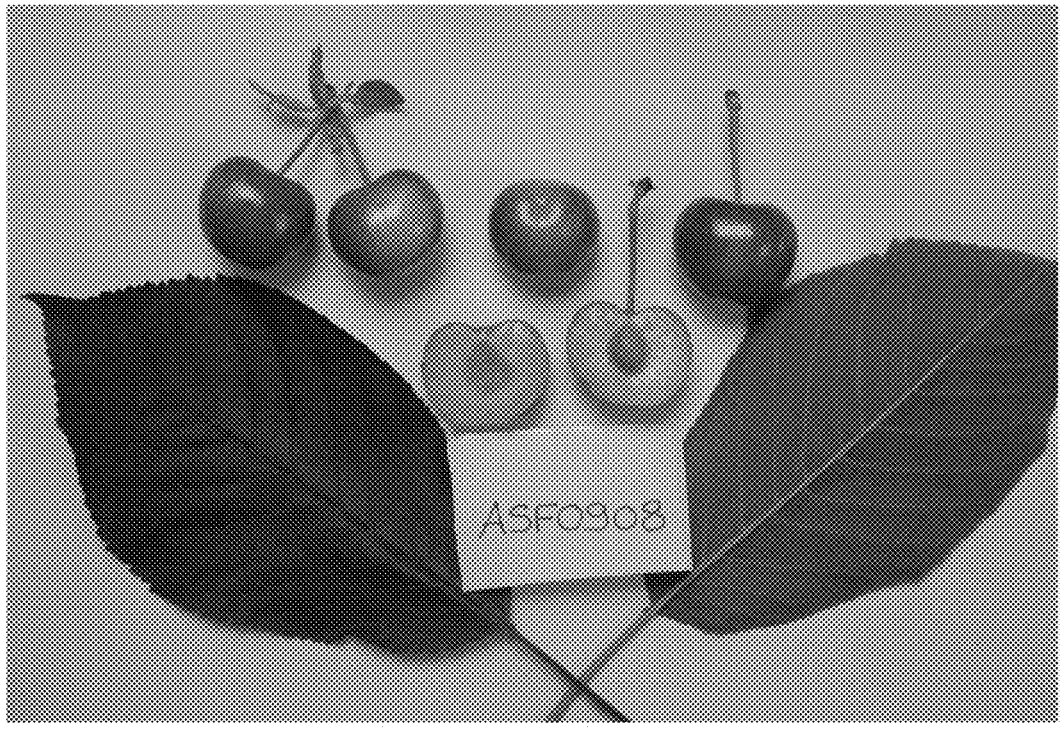
FIG. 2 is a color photograph which shows the upper and lower sides of leaves and four whole fruits of the new variety, and one fruit having been cut in a half, with the stone being left in one of the halves, for depicting the fruit flesh, the pit, and the pit cavity of the new variety.
Figure 3:
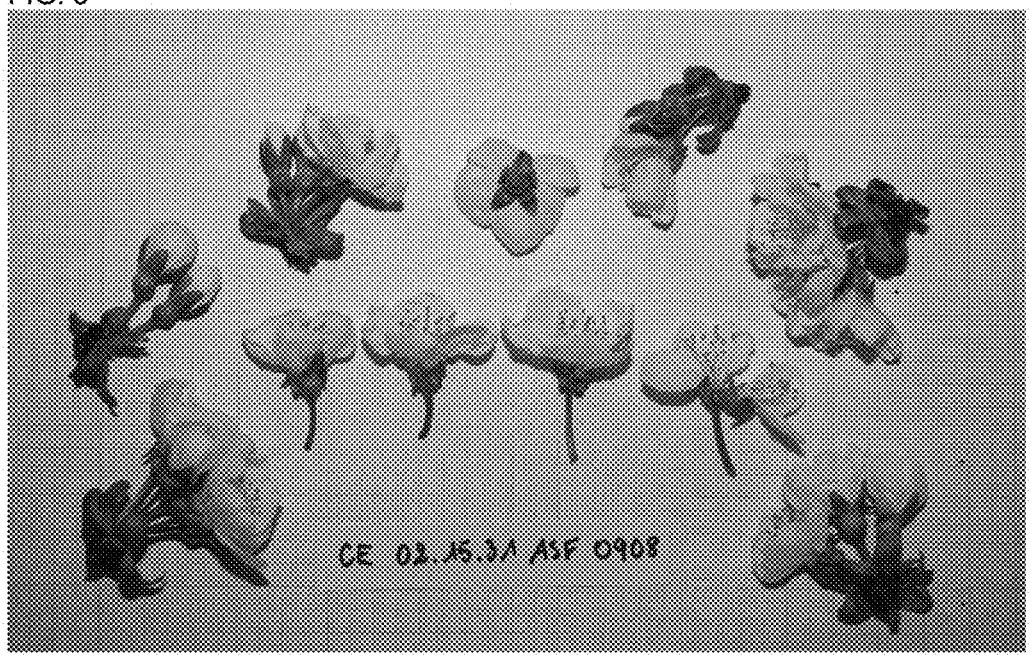
FIG. 3 shows typical white flowers of 'ROSALOLAM' variety at blooming with some leaves for depicting the flower buds at different stages of development; and the reverse and side view of the flowers and the reproductive organs with petals removed, of the new variety.
Figure 4:
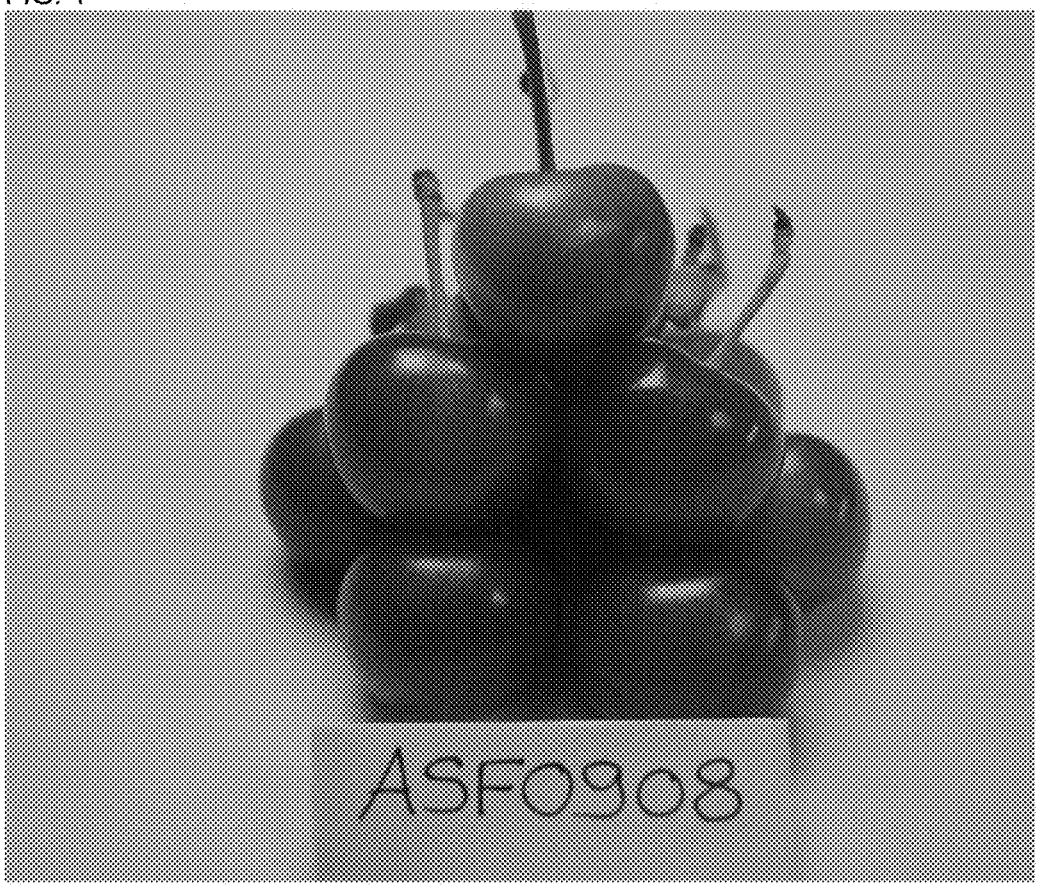
FIG. 4 is a color photograph that shows a close view of typical fruits of the new variety 'ROSALOLAM' at ripening time.

Due to chemical development, processing and printing, the leaves and fruits depicted in these photographs may or may not be accurate when compared to the actual botanical specimen.

DETAILED BOTANICAL DESCRIPTION OF THE VARIETY

The following is a detailed botanical description of the new variety of cherry tree, its flowers, foliage and fruit, as based on observations of specimens grown near Elne, South of France, with color in accordance with The R.H.S. Color Chart (Fourth Edition) provided by The Royal Horticultural Society of Great Britain.

The trees, flowers and fruits may vary in slight detail due to variations in soil type, cultural practices and climatic conditions.

The main characteristics of this new variety of sweet cherry are a big fruit size with a two colored skin considered pinkish red on an orange cream background. The color of fruit flesh is yellow to yellow orange. The fruit is very firm.

The time of beginning of flowering is medium just as the time of beginning of fruit ripening.

In comparison with the cherry tree 'RAINIER' (non-patented), the present variety 'ROSALOLAM' ripens generally approximately two weeks earlier, sometimes even more than two weeks. The flavor of the variety named 'RAINIER' is considered sugary whereas the flavor of the new variety 'ROSALOLAM' is semi-sweet and very sugary, with a brix comprised between 16 and 20 degrees. Moreover, the new variety 'ROSALOLAM' is more attractively colored than the 'RAINIER' variety. Finally, the 'ROSALOLAM' variety produces fruits that are heavier, with a weight of approximately 10 to 11 grams, compared with the 'RAINIER' variety fruits that are lower in weight and a bigger size.

DETAILED DESCRIPTION

Referring more specifically to the pomological details of this new and distinct variety of cherry tree, the following has been observed on trees on their fifth growing season (fourth year of production) under the ecological conditions prevailing at the orchards located near the town of Elne, Pyrénées-Orientales department, France.

All observations have been done on rootstock cultivar. The rootstock was a 'MAXMA14' tree. All major color code designations are by reference to The R.H.S. Colour Chart 2001 (Fourth Edition) provided by The Royal Horticultural Society of Great Britain.

Tree:

Generally: The first year the cherry tree is generally cut at 2.50 meters height. The length in one year for each lateral shoot varies from 0.60 meters to 0.80 meters. We are cutting the cherry trees during the second year to a height of 2.50 meters. The form of the cheery trees is cylindrical and the diameter is limited to 2 meters.

*Size*.—Medium to high as compared to other commercial sweet cherry cultivars. The tree size the first year was approximately 2.50 meters. The tree was pruned during each following dormant season to a height of approximately 2.50 meters. Current season's shoots growth could reach 0.80 meters. So the tree size from the second year (second and next years) reached a final height of 3.10 to 3.30 meters with current seasons shoots length comprised. The mature branches have been pruned to a length of 30.0 centimeters in order to place nets on the trees.

*Spread*.—Approximately 2.0 meters with a cylindrical shape. The whole orchard was oriented to a central leader organization, with tree lines spaced of 4.0 meters and trees spaced of 1 meter in a same tree line.

*Vigor*.—Medium, tree growth reaching 0.60 to 0.80 meters the first growing season.

*Productivity*.—Good to very good productivity, every year. The new variety produces adequate fruit set annually on a regular basis. The number of the fruit set varies with the prevailing climatic conditions and cultivar practices employed during the bloom period, and is therefore not distinctive of the present variety.

*Bearer*.—Very regular and quantitative. The extinction of the clusters of May improves the size and firmness of the fruit.

*Form*.—Naturally spreading to semi-upright.

*Hardiness*.—Hardy in all stone fruit growing areas of France and especially where the chilling requirement is between 350 and 1200 hours. No injury with a temperatures as low as −12° C. in winter. Good resistance to late frosts.

Trunk:

*Size*.—Medium. Approximately 140 millimeters above 20.0 centimeters from ground, on $5^{th}$ growing season.

*Bark texture*.—Smooth with reliefs due to the lenticels.

*Lenticels*.—High number of lenticels. The number of lenticels reaches 28 to 35 lenticels per 10 $cm^2$. At the $5^{th}$ growing season, lenticels are 3.0 to 4.5 millimeters in height and 9.0 to 16.0 millimeters in width.

*Lenticels color*.—Color of lenticels is RHS Greyed Orange 164 A.

*Bark color*.—Grey silver brown (RHS BROWN 200 B).

Branches:

*Size*.—Medium for the branches at the $5^{th}$ growing season.

*Diameter*.—Average diameter of 52.0 to 63.0 millimeters.

*Surface texture*.—Smooth with lenticels. The number of lenticels reaches 28 to 35 lenticels per 10 $cm^2$. Lenticels are 3.0 to 4.5 millimeters in height and 9.0 to 16.0 millimeters in width. The color of lenticels is RHS GREYED ORANGE 164 A. Wood that is several years old has no furrowed appearance.

*Color*.—Old growth is brown (RHS BROWN 200 B).

Current season shoots:

*Size*.—Medium for the new growth, between 50.0 and 75.0 centimeters.

*Diameter*.—Average diameter from 6.0 to 8.0 millimeters.

*Surface texture*.—Smooth. Wood that is several years old has no furrowed appearance.

*Crotch angles*.—Primary branches are considered variable, but the crotch angles are generally between 75 degrees and 90 degrees from the horizontal axis. This particular characteristic is not considered distinctive of the variety, however.

*Internode*.—Generally from 80.0 millimeters to 90.0 millimeters length.

*Color*.—New growth is orange brown (RHS GREYED ORANGE 165 A or RHS GREYED ORANGE 177 A).

Leaves:

*Size*.—Medium to large for the species. Leaf measurements have been taken from vigorous, upright, current-season growth at approximately mid-shoot. The ratio leaf length/leaf width is 1.91.

*Length*.—From 127.0 to 142.0 millimeters with leaf petiole. Average length with petiole 137.1 millimeters.

*Width*.—From 64.0 to 77.0 millimeters. Average width 71.6 millimeters.

*Leaf form in cross view*.—Concave.

*Leaf form*.—Lanceolate with an elliptic shape.

*Apex*.—Acuminate.

*Leaf base*.—Round.

Leaf color:

*Upper leaf surface*.—Dark green (RHS GREEN GROUP 137 A) to a lighter green (RHS YELLOW GREEN 147 A).

*Lower surface*.—A lighter green than the upper leaf surface (RHS YELLOW GREEN 146 A or RHS YELLOW GREEN 147 B).

*Leaf texture*.—Smooth. The lower surface is also smooth.

*Leaf venation*.—Pinnately veined.

Mid-vein:

*Color*.—Light green with a yellow touch (RHS YELLOW GREEN 144 C or RHS YELLOW GREEN 145 A to RHS YELLOW GREEN 145 B) and evolves with maturity.

*Leaf margins*.—Undulating.

*Form*.—Considered dentate.

*Uniformity*.—Leaves are identical.

Leaf petioles:

*Size*.—Considered medium to long.

*Length*.—About 42.0 to 53.0 millimeters.

*Diameter*.—About 2.0 millimeters.

*Color*.—Upper surface orange (RHS GREYED ORANGE 166 A). Lower surface light green (RHS YELLOW GREEN 144 B).

*Ratio blade length/petiole length*.—More or less 2.89.

Leaf glands:

*Size*.—Considered small. Their length is about 1.5 millimeters.

*Number*.—Generally 2.

*Type*.—Reniform.

*Diameter*.—Approximately 1.5 millimeters.

*Color*.—Light yellow (RHS GREYED YELLOW 161 A) to almost red (RHS RED GROUP 53 A), depending on the leave's age.

Leaf stipules:

*Generally*.—No leaf stipules were observed.

Flowers:

Flower buds:

*Generally*.—At pre-floral stage of development, the floral bunches are make up with 4 to 6 floral buds having a conic shape with a round tip. Their form is evolving until blooming, with variables dimensions. Just before blooming, floral buds have a diameter of about 8.5 millimeters wide and are approximately 16.0 millimeters long.

*Color*.—This characteristic is dependent upon the proximity to bloom. At pre-floral stage of development, the bottom of the flowers buds, or calyx formed by sepals, is of green or light green color (RHS GREEN 138 A or RHS YELLOW GREEN 144 A to RHS YELLOW GREEN 144 B) with purple pink areas (RHS GREYED RED GROUP 178 A to RHS GREYED RED GROUP 178 B); the corolla formed by petals, is generally pure white (RHS WHITE 155 D) on both upper and lower surfaces.

*Hardiness*.—The buds are considered hardy under typical central Pyrénées-Orientales department climatic conditions. No winter injury was noted during the last several years of evaluation in the central Pyrénées-Orientales department, with winter temperatures as low as −10° C. in January. The current variety has not been intentionally subjected to drought or heat stress, but the variety showed a very good resistance in orchard to temperatures up to 42° C. with an average temperature between 28° C. and 30° C. during 3 weeks in summer.

*Date of bloom*.—Generally late March or early in April. The first bloom was observed on March 31$^{st}$ until Apr. 10$^{th}$, 2010. Last sixth blooms took place respectively from March 18$^{th}$ until Mar. 30$^{th}$, 2011, March 29$^{th}$ until Apr. 8$^{th}$, 2012, from April 3$^{rd}$ to Apr. 13$^{th}$, 2013, from March 27$^{th}$ to Apr. 4$^{th}$, 2014, from April 5$^{th}$ to Apr. 14$^{th}$, 2015 and from March 27$^{th}$ until Apr. 8$^{th}$, 2016.

*Blooming time*.—Considered medium relative comparison to other commercial cherry cultivars grown in the Pyrénées-Orientales department, France. The date of full bloom is observed at the middle of the blooming period. The date of bloom varies slightly with climatic conditions and cultural practices.

*Blooming period*.—Average 10-13 days. This characteristic varies slightly with the prevailing climatic conditions.

*Flower type*.—The variety is considered to have a showy type flower.

*Flower size*.—Considered medium. Average diameter between 23.0 and 28.0 millimeters when totally opened.

*Bloom quantity*.—Considered abundant or very abundant, approximately 60 flowers per meter.

*Flower bud frequency*.—Generally 4 to 6 flower buds appear per node.

Petal:

*Size*.—Considered small for the species.

*Length*.—Generally about 16.0 millimeters.

*Width*.—Generally about 15.0 millimeters.

*Petal form*.—Large form, elliptic, usually slightly overlapping.

*Petal count*.—Nearly always 5.

*Petal texture*.—Both petal surfaces have a smooth texture.

*Petal margins*.—Smooth.

*Petal color*.—Pure white color (RHS WHITE 155 D) on both surfaces.

*Fragrance*.—Very soft.

Petal claw:

*Form*.—The claw is considered to have a conic form with a slightly rounded tip.

*Length*.—Approximately 7.0 millimeters.

*Width*.—Approximately 4.0 millimeters.

Petal apex:

*Generally*.—The petal apices are generally wide dome shaped.

Flower pedicel:

*Length*.—Considered medium to long and having an average length of approximately 16.0 to 20.0 millimeters.

*Diameter*.—Average 1.5 millimeter.

*Color*.—Green (RHS YELLOW GREEN 144 A to RHS YELLOW GREEN B).

Calyx:

*Internal surface texture*.—Smooth.

*Color*.—The upper surface is of green or light green color (RHS GREEN 138 A or RHS YELLOW GREEN 144 A to RHS YELLOW GREEN 144 B) with purple pink areas (RHS GREYED RED GROUP 178 A to RHS GREYED RED GROUP 178 B). The lower surface is of light green color (RHS YELLOW GREEN 144 B to RHS YELLOW GREEN 144 C).

Sepals:

*Surface texture*.—The outer and inner surfaces of the sepals have a smooth texture.

*Size*.—Usually considered medium.

*Length*.—Approximately 6.0 millimeters.

*Width*.—Approximately 5.0 millimeters.

*Shape*.—Elliptic shape.

*Color*.—The upper surface is green or light green (RHS GREEN 138 A or RHS YELLOW GREEN 144 A to RHS YELLOW GREEN 144 B) with purple pink zones (RHS GREYED RED 178 A to RHS GREYED RED 178 B). The lower surface is green (RHS YELLOW GREEN 144 B to RHS YELLOW GREEN 144 C).

*Number of sepals*.—Generally 5, no overlapping.

*Sepal apex and margin*.—Elliptic in shape with a slightly rounder apex.

*Average number of stamens per flower*.—Between 30 and 40 stamens per flower.

*Stamen size compared to petals*.—The size of stamen is smaller than the size of petals.

Anthers:

*Length*.—Medium. Approximately 14.0 millimeters.

*Form*.—Cardioid.

*Color*.—Yellow orange red color (RHS GREYED ORANGE 163 B to RHS GREYED ORANGE 163 C). The color evolves with flowering.

*Pollen production*.—Pollen is abundant, and has a yellow color (RHS YELLOW ORANGE 17 B to RHS YELLOW ORANGE 17 C or RHS YELLOW ORANGE 9 A) that varies with maturity. The fertility has been checked and the 'ROSALOLAM' variety is not self-fertile (or self pollinating). However, because of the considerable amount of pollen that is product, the pollination is performed as expected.

Filaments:

*Size*.—Variable in length, approximately between 6.0 and 14.0 millimeters in length, smaller than pistil's length.

*Color*.—Considered as white (RHS WHITE 155 D).

Pistil:

*Number*.—Usually 1.

*Length*.—Approximately from 15.0 to 18.0 millimeters including the ovary, that is longer than stamens length.

*Color*.—Considered very pale green (RHS YELLOW GREEN 149 B to RHS YELLOW GREEN 149 C). The color is evolving with flowering.

*Surface texture*.—Glabrous.

*Pubescence*.—Absent.

*Stigma*.—Approximately 1.1 millimeter in diameter, with an elliptic shape and a light green color (RHS YELLOW GREEN N 144 A to RHS YELLOW GREEN N 144 B).

*Ovary*.—Approximately 2.9 millimeters in height. The diameter of the ovary is about 1.8 millimeters. The color is considered green (RHS GREEN 143 A).

Type of reproduction: Pollination.

Pollinator: The following variety is a good pollinator: 'RED-LAM' cherry tree (U.S. Plant patent application Ser. No. 15/330,879).

Fruits:

*Maturity when described*.—Firm at maturity.

*Date of first picking*.—May 29$^{th}$, 2009. The date of picking varies slightly with climatic conditions.

*Date of last picking*.—Last known picking times carry on from May 29$^{th}$ to Jun. 6$^{th}$, 2009, then from June 1$^{st}$ to Jun. 8$^{th}$, 2010, then from May 21$^{st}$ to May 28$^{th}$, 2011, then from June 6$^{th}$ to Jun. 13$^{th}$, 2012, then from June 13$^{th}$ to Jun. 22$^{nd}$, 2013, then from May 17$^{th}$ to May 26$^{th}$, 2014, then from May 30$^{th}$ to Jun. 9$^{th}$, 2015 and then from June 3$^{rd}$ to Jun. 10$^{th}$, 2016.

*Ripening period*.—Approximately 8 to 11 days.

Size:

*Generally*.—Considered big, with a homogeneous size between them.

*Medium size*.—29-30 millimeters.

*Average cheek diameter*.—About 27.0 to 29.0 millimeters.

*Average axial diameter*.—About 22.0 to 25.0 millimeters.

*Typical weight*.—Generally about 11.2 grams. This characteristic is highly dependent upon the prevailing cultural practices, and therefore is not particularly distinctive of the variety.

Fruit form:

*Generally*.—Reniform.

*Fruit suture*.—Not marked.

Ventral surface:

*Form*.—Smooth.

*Apex*.—Slightly in depression.

*Base*.—Slightly in depression.

*Stem cavity*.—Average depth of the stem cavity is about 1.5 to 2.0 millimeters. Average width is about 4.0 to 5.0 millimeters.

Fruit skin:

*Thickness*.—Considered smooth and medium to thin thick, and tenacious to the flesh depending on stage of maturity.

*Tenacity*.—Tenacious to flesh.

*Texture*.—Smooth.

*Taste*.—Sweet.

*Tendency to crack*.—None.

Color:

*Blush color*.—The color of the fruit is considered two colored. The fruit skin is colored on 60% of its surface in pinkish red (RHS RED GROUP 46 A) on an orange cream background (RHS YELLOW GROUP 11 A or RHS YELLOW GROUP 13 C).

*Fruit stem*.—Medium to short in length, approximately 25.0 to 35.0 millimeters.

*Diameter*.—Approximately 1.5 millimeters.

*Color*.—Light green (RHS YELLOW GREEN GROUP 144 D).

Flesh:

*Ripens*.—Homogenous and regular.

*Texture*.—Very crunchy, luscious, juicy.

*Fibers*.—No fibers.

*Firmness*.—Considered firm.

*Aroma*.—Pronounced aroma.

*Eating quality*.—Very good, very sweet, aromatic.

*Flavor*.—Semi-sweet, very sugared, aromatic. Low acidic level. Juicy and aromatic.

*Juice*.—Large amount, very juicy.

*Brix*.—Approximately 16.5 degrees, varies slightly with amount of fruit per tree and climatic conditions.

*Color*.—From a yellow color (RHS YELLOW 11 B or RHS YELLOW 11 C) to an orange yellow color (RHS YELLOW ORANGE 18 B) at ripening time.

Stone:

*Type*.—Free stone to semi-freestoneat fruits picking.

*Size*.—Medium for the variety.

*Length*.—Average 10.0 millimeters.

*Width*.—Average width 8.5 millimeters.

*Diameter*.—Average diameter 7 millimeters.

*Form*.—Round to ovate.

*Base*.—Generally round to slanting.

*Apex*.—Round.

*Stone cavity*.—Medium with a form and dimensions corresponding to the stone's dimensions.

Stone surface:

*Surface texture*.—Smooth.

*Ridges*.—None, smooth.

*Tendency to split*.—Splitting is absent.

Ventral edge:

*Width*.—Very shallow, more or less 1.0 millimeter.

Dorsal edge:

*Shape*.—Full, with a slight relief.

*Stone color*.—The color of the dry stone is light yellow (RHS YELLOW WHITE 158 A) to yellow (RHS GREYED YELLOW 161 D).

*Tendency to split*.—None.

Kernel:

*Size*.—Medium.

*Length*.—About 7.5 millimeters.

*Width*.—About 5.0 millimeters.

*Thickness*.—About 3.5 millimeters.

*Form*.—Elliptic with a round-shaped apex and a pointed base.

*Pellicle*.—Not pubescent.

*Color*.—The kernel skin is orange brown (RHS GREYED YELLOW 161 B). The kernel and its embryo are mature at the time of fruit maturity.

Use: Dessert. Fresh products.

*Market*.—Local and long distance. On the tree fruits can stay 10 days while keeping good gustative qualities. The lifetime after picking is also good.

Keeping quality: Good, held well for 30 days in cold storage at 2° C. and maintained good appearance and eating quality.

Shipping quality: Good, showed minimal bruising or scarring during picking, packing and shipping trials.

Plant/fruit disease resistance/susceptibility: Specific tests were run with regards to *Monilia* and 'ROSALOLAM' variety seems to be low sensitive to *Monilia*. Moreover 'ROSALOLAM' is low sensitive to other observed pathologies, to rupture and to conservation pathologies.

The present new variety of cherry tree, its flowers, foliage and fruit herein described may vary in slight detail due to climate, soil conditions and cultural practices under which the variety may be grown. The present description is that of the variety grown under the ecological conditions prevailing near Elne, Pyrénées Orientales (66), France (FR).

We claim:

1. A new and distinct variety of cherry tree, substantially as illustrated and described, characterized by its early ripening, its fruit and especially by its big size, its two colored fruit skin, its firmness, good flavor and eating quality; the fruit is further characterized by its good handling and storage qualities.

* * * * *